United States Patent
Borchert et al.

(10) Patent No.: US 10,767,220 B2
(45) Date of Patent: Sep. 8, 2020

(54) METHODS OF AMPLIFYING NUCLEIC ACIDS AND COMPOSITIONS FOR PRACTICING THE SAME

(71) Applicant: Becton, Dickinson and Company, Franklin Lakes, NJ (US)

(72) Inventors: Kristen Mary Borchert, Apex, NC (US); Frances Poyen Tong, Carrboro, NC (US); Charlotte Ann Brown, Chapel Hill, NC (US); Richard Lee Kelley, Durham, NC (US); Chang Chen, Cary, NC (US); Jeffrey Propse Baker, Durham, NC (US); Liwen Stacy Xu, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 173 days.

(21) Appl. No.: 15/563,939

(22) PCT Filed: May 17, 2016

(86) PCT No.: PCT/US2016/032919
§ 371 (c)(1),
(2) Date: Oct. 2, 2017

(87) PCT Pub. No.: WO2016/187224
PCT Pub. Date: Nov. 24, 2016

(65) Prior Publication Data
US 2018/0127817 A1    May 10, 2018

Related U.S. Application Data

(60) Provisional application No. 62/164,871, filed on May 21, 2015.

(51) Int. Cl.
*C12Q 1/68*    (2018.01)
*C12Q 1/6869*    (2018.01)
*C12Q 1/686*    (2018.01)

(52) U.S. Cl.
CPC .......... *C12Q 1/6869* (2013.01); *C12Q 1/686* (2013.01); *C12Q 2535/122* (2013.01); *C12Q 2537/143* (2013.01)

(58) Field of Classification Search
None
See application file for complete search history.

(56) References Cited

U.S. PATENT DOCUMENTS

| | | |
|---|---|---|
| 2012/0039887 A1 * | 2/2012 | Rubin ............... C07K 14/4748 424/137.1 |
| 2013/0338933 A1 | 12/2013 | Deciu et al. |
| 2014/0206543 A1 * | 7/2014 | Rogan ................ C12Q 1/6886 506/2 |
| 2014/0256571 A1 | 9/2014 | Konvicka |

FOREIGN PATENT DOCUMENTS

| | | | | |
|---|---|---|---|---|
| WO | WO-2012058689 A2 * | 5/2012 | ........... | C12Q 1/6883 |
| WO | WO-2015157571 A1 * | 10/2015 | ........... | C12Q 1/6883 |

OTHER PUBLICATIONS

Molyneux et al. (Nature Genetics, 2014, 46(9):964-972) (Year: 2014).*
Molyneux et al. (Nature Genetics, 2014, 46(9):964-973, IDS reference) (Year: 2014).*
McLysaght et al. (PNAS, 2014, vol. 111, No. 1, p. 361-366, IDS reference) (Year: 2014).*
Makino, et al., "Genome-wide deserts for copy number variation in vertebrates", Nature Communications, 4:2283, pp. 1-10, 2013.
McLysaght, et al., "Ohnologs are overrepresented in pathogenic copy number mutations", PNAS Jan. 7, 2014. 111 (1) 361-366.

* cited by examiner

*Primary Examiner* — Stephanie K Mummert
(74) *Attorney, Agent, or Firm* — Bret E. Field; Bozicevic, Field & Francis LLP

(57) ABSTRACT

Provided are methods of amplifying nucleic acids. The methods include combining a nucleic acid sample and one or more amplification primers adapted to amplify a region of one or more copy number stable genes in a reaction mixture under conditions sufficient to amplify the one or more copy number stable genes. Aspects of the present disclosure further include compositions and kits that find use in practicing embodiments of the methods.

20 Claims, 3 Drawing Sheets

FIG. 1

| Gene | Chr. | Start (bp) | End (bp) | Displaying CNV (Q) Ohnolog (O) | Distance to ohnolog (bp) | Num_Am plicons | Total_Ba ses | Covered_ Bases | Missed_ Bases | Overall B_ average | Overall C_ average | Num_Exo ns | Comments |
|---|---|---|---|---|---|---|---|---|---|---|---|---|---|
| HNRNPR | chr1 | 23,608,663 | 23,643,440 | O | NA | 27 | 2318 | 2187 | 131 | 0.9435 | 0.9435 | 12 | Heterogeneous Nuclear Ribonucleoprotein R; Ubiquitous; involved in mRNA processing |
| TCEB3 | chr1 | 23,842,549 | 23,903,574 | | 31,259 | 23 | 2507 | 2267 | 240 | 0.9043 | 0.9043 | 11 | Transcription Elongation Factor B (SIII), Polypeptide 3 (110kDa, elongin A); associated with Lung Cancer |
| IL22RA1 | chr1 | 24,310,848 | 24,342,100 | | 7,506 | 19 | 1795 | 1593 | 202 | 0.8875 | 0.8875 | 7 | Interleukin 22 Receptor, Alpha 1; associated with Melanoma |
| RCAN3 | chr1 | 24,701,974 | 24,736,891 | O | NA | 9 | 1257 | 1211 | 46 | 0.9634 | 0.9634 | 7 | RCAN Family Member 3; Associated with CLL and Adenocarcinoma |
| GJB5 | chr1 | 34,893,236 | 34,906,700 | O | NA | 8 | 832 | 802 | 23 | 0.965 | 0.965 | 1 | Gap Junction Protein, Beta 5, 31.1kDa; Associated with NSCLC |
| SLC25A44 | chr1 | 154,400,520 | 154,449,210 | | 15,386 | 10 | 975 | 932 | 43 | 0.955 | 0.955 | 3 | Solute Carrier Family 25, Member 44; mitochondrial carrier protein |
| MT3 | chr16 | 56,190,708 | 56,192,500 | | 340,749 | 4 | 227 | 227 | 0 | 1 | 1 | 3 | Metallothionein 3; Associated with Breast and Prostate Cancer |
| MT1X | chr16 | 56,267,600 | 56,275,600 | | 247,841 | 3 | 216 | 216 | 0 | 1 | 1 | 3 | Metallothionein 1X; Associated with multiple cancers |
| NUP93 | chr16 | 56,321,573 | 56,435,177 | | 87,072 | 40 | 2800 | 2772 | 28 | 0.99 | 0.99 | 22 | Nucleoporin 93kDa |
| RABL2B | chr22 | 49,662,796 | 49,968,957 | O | NA | 12 | 1010 | 1010 | 0 | 1 | 1 | 10 | RAB, member of RAS oncogene family-like 2B; member of RAS superfamily |

Example Custom NGS Panel

Makino et al. (2013)

FIG. 3

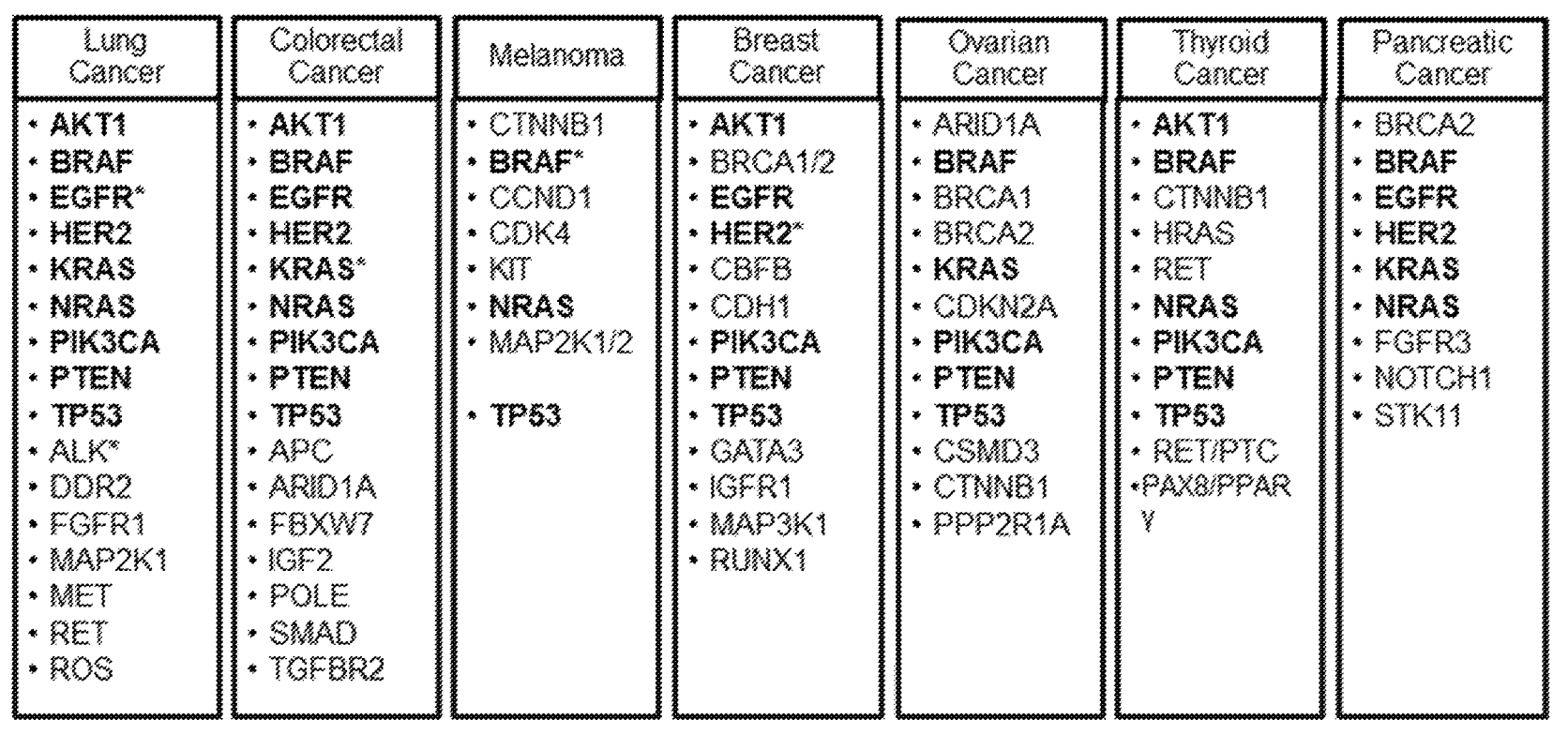

| Lung Cancer | Colorectal Cancer | Melanoma | Breast Cancer | Ovarian Cancer | Thyroid Cancer | Pancreatic Cancer |
|---|---|---|---|---|---|---|
| • AKT1 | • AKT1 | • CTNNB1 | • AKT1 | • ARID1A | • AKT1 | • BRCA2 |
| • BRAF | • BRAF | • BRAF\* | • BRCA1/2 | • BRAF | • BRAF | • BRAF |
| • EGFR\* | • EGFR | • CCND1 | • EGFR | • BRCA1 | • CTNNB1 | • EGFR |
| • HER2 | • HER2 | • CDK4 | • HER2\* | • BRCA2 | • HRAS | • HER2 |
| • KRAS | • KRAS\* | • KIT | • CBFB | • KRAS | • RET | • KRAS |
| • NRAS | • NRAS | • NRAS | • CDH1 | • CDKN2A | • NRAS | • NRAS |
| • PIK3CA | • PIK3CA | • MAP2K1/2 | • PIK3CA | • PIK3CA | • PIK3CA | • FGFR3 |
| • PTEN | • PTEN | • TP53 | • PTEN | • PTEN | • PTEN | • NOTCH1 |
| • TP53 | • TP53 |  | • TP53 | • TP53 | • TP53 | • STK11 |
| • ALK\* | • APC |  | • GATA3 | • CSMD3 | • RET/PTC |  |
| • DDR2 | • ARID1A |  | • IGFR1 | • CTNNB1 | • PAX8/PPAR γ |  |
| • FGFR1 | • FBXW7 |  | • MAP3K1 | • PPP2R1A |  |  |
| • MAP2K1 | • IGF2 |  | • RUNX1 |  |  |  |
| • MET | • POLE |  |  |  |  |  |
| • RET | • SMAD |  |  |  |  |  |
| • ROS | • TGFBR2 |  |  |  |  |  |

METHODS OF AMPLIFYING NUCLEIC ACIDS AND COMPOSITIONS FOR PRACTICING THE SAME

CROSS-REFERENCE TO RELATED APPLICATIONS

Pursuant to 35 U.S.C. § 119(e), this application claims priority to the filing date of U.S. Provisional Patent Application Ser. No. 62/164,871, filed May 21, 2015, the disclosure of which application is incorporated herein by reference.

INTRODUCTION

Nucleic acid sequencing methods include the Sanger "dideoxy" method that relies upon the use of dideoxyribonucleoside triphosphates as chain terminators. The Sanger method has been adapted for use in automated sequencing with the use of chain terminators incorporating fluorescent labels. Other methods include "next-generation" sequencing methods, including those based on successive cycles of incorporation of fluorescently labeled nucleic acid analogues. In such "sequencing by synthesis" or "cycle sequencing" methods the identity of the added base is determined after each nucleotide addition by detecting the fluorescent label. Other next-generation sequencing methods include those based on the detection of hydrogen ions that are released during the polymerization of DNA. A microwell containing a template DNA strand to be sequenced is flooded with a single species of deoxyribonucleotide triphosphate (dNTP). If the introduced dNTP is complementary to the leading template nucleotide, it is incorporated into the growing complementary strand. This causes the release of a hydrogen ion that triggers an ISFET ion sensor, which indicates that a reaction has occurred. If homopolymer repeats are present in the template sequence, multiple dNTP molecules will be incorporated in a single cycle. This leads to a corresponding number of released hydrogens and a proportionally higher electronic signal.

Copy number variations (CNVs) are alterations observed in the genome that result in genes having an abnormal number of copies—either more or less than the expected number of two. CNVs may be indicative of large-scale chromosomal rearrangements, such as large insertions or deletions, which can be commonly found in cancer tissue. In some cases, entire chromosomes can be lost or duplicated, which is a common cause of genetic disorders, such as Down syndrome (trisomy 21), cat eye syndrome (trisomy 22), Williams syndrome (monosomy 7), and various others. Identifying copy number variations can help understand and diagnose cancer and aneuploidy-related disorders.

CNVs play a large role in cancer and detection of altered numbers of copies of certain genes can provide physicians with information to guide therapy. Historically, CNVs have been detected with cytogenetic techniques such as array-based comparative genome hybridization and molecular techniques such as SNP arrays. More recently, detection of CNVs by next-generation sequencing (NGS) has proven feasible, enabling researchers to detect three major categories of genomic alteration—single-nucleotide polymorphisms (SNPs), insertions/deletions, and CNVs in one assay platform.

SUMMARY

Provided are methods of amplifying nucleic acids. The methods include combining a nucleic acid sample and one or more amplification primers adapted to amplify a region of one or more copy number stable genes in a reaction mixture under conditions sufficient to amplify the one or more copy number stable genes. Aspects of the present disclosure further include compositions and kits that find use in practicing embodiments of the methods.

BRIEF DESCRIPTION OF THE FIGURES

FIG. 1 provides next generation sequencing (NGS) data obtained using a custom NGS sequencing panel according to one embodiment of the present disclosure. In this example embodiment, a sequencing library was prepared using a panel of primers adapted to amplify ten distinct copy number stable genes, as well as genes of interest present in the sample.

FIG. 3 shows non-limiting examples of genes which may be amplified, e.g., as part of preparing an NGS sequencing library, according to certain aspects of the present disclosure.

DETAILED DESCRIPTION

Figure 2:
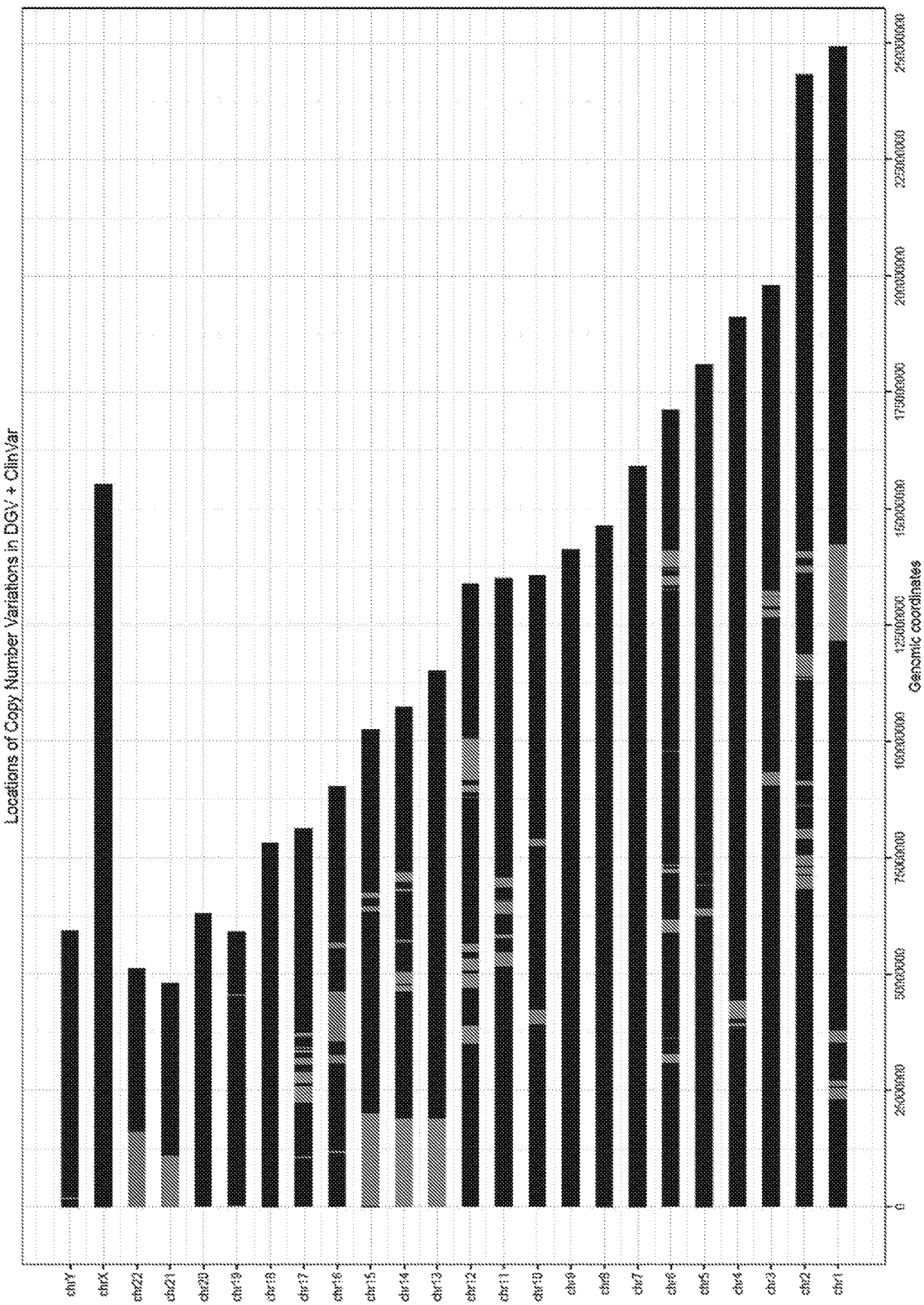
FIG. 2 graphically illustrates copy number stable regions of the human genome identified using an approach according to one embodiment of the present disclosure.

Provided are methods of amplifying nucleic acids. The methods include combining a nucleic acid sample and one or more amplification primers adapted to amplify a region of one or more copy number stable genes in a reaction mixture under conditions sufficient to amplify the one or more copy number stable genes. Aspects of the present disclosure further include compositions and kits that find use in practicing embodiments of the methods.

Before the methods, compositions and kits of the present disclosure are described in greater detail, it is to be understood that the methods, compositions and kits are not limited to particular embodiments described, as such may, of course, vary. It is also to be understood that the terminology used herein is for the purpose of describing particular embodiments only, and is not intended to be limiting, since the scope of the methods, compositions and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, compositions and kits. The upper and lower limits of these smaller ranges may independently be included in the smaller ranges and are also encompassed within the methods, compositions and kits, subject to any specifically excluded limit in the stated range. Where the stated range includes one or both of the limits, ranges excluding either or both of those included limits are also included in the methods, compositions and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, compositions and kits belong. Although any methods, compositions and kits similar or equivalent to those described herein can also be used in the practice or testing of the methods, compositions and kits, representative illustrative methods, compositions and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, compositions and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, compositions and kits, which are, for clarity, described in the context of separate embodiments, may also be provided in combination in a single embodiment. Conversely, various features of the methods, compositions and kits, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions/kits. In addition, all sub-combinations listed in the embodiments describing such variables are also specifically embraced by the present methods, compositions and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods, compositions and kits. Any recited method can be carried out in the order of events recited or in any other order that is logically possible.

Methods

Aspects of the present disclosure include methods of amplifying nucleic acids. The methods include combining a nucleic acid sample and one or more amplification primers adapted to amplify a region of one or more copy number stable genes in a reaction mixture under conditions sufficient to amplify the one or more copy number stable genes.

Amplification Primers

As summarized above, aspects of the invention include producing a reaction mixture from a sample and one or more amplification primers adapted to amplify a region of one or more copy number stable genes. By "copy number stable gene" is meant a gene or genomic region that is refractory to duplication or loss (e.g., is refractory to copy number variation (CNV)). For example, a copy number stable gene may be a gene or genomic region having a copy number that does not vary (or substantially vary) between a genome of interest and a reference genome. For example, a copy number stable gene may be a gene or genomic region that is present in both a genome of interest (e.g., a human tumor genome) and a reference genome (e.g., a human non-tumor genome) and, based on available information relating to the copy number of the gene, is known to not vary (or substantially vary) in copy number between the genome of interest and the reference genome.

In certain aspects, a copy number stable gene has the same copy number in 80% or more, 85% or more, 90% or more, 95% or more, 96% or more, 97% or more, 98% or more, 99% or more, or 100% of the genomes in a population of interest, e.g., humans, or human subpopulations of interest (e.g., racial/ethnic human subpopulations, or the like).

Because the copy number stable gene is refractory to duplication or loss, amplicons produced from copy number stable genes according the subject methods find use, e.g., as internal copy number controls in amplification- and/or sequencing-based assays for determining the copy number (and optionally, the presence of CNVs) in one or more genes of interest in a nucleic acid sample of interest. In certain aspects, such genes of interest are clinically relevant, e.g., genes for which copy number variation is associated with a disease or disorder, such as cancer, aneuploidy-related disorders (e.g., trisomy 21, trisomy 22, monosomy 7, etc.), and the like. As such, in certain embodiments, amplification of the one or more copy number stable genes finds use, e.g., in diagnosing a condition known to be associated with one or more CNVs. In certain aspects, the diagnosis includes sequencing (e.g., by NGS sequencing) the amplicons of the one or more copy number stable genes and one or more genes of interest to determine the copy number (and optionally, detect CNV, if any) in the one or more genes of interest.

According to certain embodiments, the one or more copy number stable genes are located in ohnolog-rich regions (ORRs) of the genome. An "ohnolog" is a duplicated gene derived from whole genome duplication (WGD). In certain aspects, an ORR is a genomic region (e.g., a human genomic region) having a proportion of ohnologs that is 50% or greater, 55% or greater, 60% or greater, 65% or greater, 70% or greater, or 75% or greater in a 2 Mb window. According to certain embodiments, the one or more copy number stable genes include one or more ohnologs. A detailed description of human ohnolog-rich regions and human ohnologs is found in Makino et al. (2013) *Nature Communications* 4:2283, and in certain aspects, one or any combination of ohnologs or copy number stable genes within the ohnolog-rich regions described therein may be amplified according to the methods of the present disclosure.

In certain aspects, the combining comprises combining a known amount of nucleic acids corresponding to one or more copy number stable genes with the nucleic acid sample and the one or more amplification primers adapted to amplify a region of the nucleic acids corresponding to one or more copy number stable genes.

The one or more amplification primers adapted to amplify a region of one or more copy number stable genes may be adapted to amplify any useful copy number stable genes, including any of the copy number stable genes described herein, e.g., ohnologs, genes or genomic regions that are refractory to duplication or loss within ohnolog-rich regions, and the like. Any amplification primer, or combination of two or more amplification primers, adapted to amplify the one or more copy number stable genes (and optionally, one or more nucleic acids of interest) may be employed. According to certain embodiments, the one or more amplification primers are adapted to amplify one, each of, or any combination of the copy number stable genes HNRNPR (Entrez Gene ID 10236), TCEB3 (Entrez Gene ID 6924), IL22RA1 (Entrez Gene ID 58985), RCAN3 (Entrez Gene ID 11123), GJB5 (Entrez Gene ID 2707), SLC25A44 (Entrez Gene ID 9673), MT3 (Entrez Gene ID 4504), MT1X (Entrez Gene ID 4501), NUP93 (Entrez Gene ID 9688) and/or RABL2B (Entrez Gene ID 11158).

In certain aspects, the one or more amplification primers are non-random primers specifically designed/selected to amplify one or more predetermined copy number stable genes, and optionally, one or more predetermined nucleic acids of interest in the sample. For example, the one or more amplification primers may be designed/selected by a practitioner of the subject methods based both on the type of nucleic acid sample that will be present in the reaction mixture. By way of example, when the nucleic acid sample is a human genomic DNA sample, the one or more amplification primers may be designed/selected by the practitioner to ensure that the one or more amplification primers are adapted to amplify one or more copy number stable genes present in the human genome. CNVs are known to occur in organisms other than humans, such as rodents (e.g., mice and rats), dogs, cattle, rhesus monkeys, chimpanzees, and birds. When the nucleic acid sample is isolated from a non-human organism, the one or more amplification primers may be designed/selected to amplify copy number stable genes present in the genome of the relevant non-human organism.

According to certain embodiments, a "panel" (or "pool") of two or more amplification primers is employed. Such pools find use, e.g., when multiplexed amplification of two or more copy number stable genes is desirable. In certain embodiments, a panel of primers is employed and adapted to amplify 2 or more, 3 or more, 4 or more, 5 or more, 6 or more, 7 or more, 8 or more, 9 or more, 10 or more, 15 or more, 20 or more, 25 or more, 30 or more, 40 or more, 50 or more, or 100 or more copy number stable genes. Such pools may additionally include primers adapted to amplify one or more genes of interest, e.g., genes for which it is desirable to determine copy number information (e.g., for detecting CNV, if any), including but not limited to, genes for which copy number variation is associated with a disease or disorder (e.g., cancer or a particular type thereof, any aneuploidy-related disorder, etc.). As such, according to certain embodiments of the methods of the present disclosure, a panel of primers may be employed that is adapted to amplify any desirable number of copy number stable genes, and additionally, adapted to amplify any desirable number of genes of interest, including but not limited to, 1 or more, 2 or more, 3 or more, 4 or more, 5 or more, 6 or more, 7 or more, 8 or more, 9 or more, 10 or more, 15 or more, 20 or more, 25 or more, 30 or more, 40 or more, 50 or more, 100 or more, 150 or more, 200 or more, 250 or more, 500 or more, or 1000 or more genes of interest. In addition to detection of CNV and the like, amplification of such genes of interest finds use, e.g., for SNP genotyping/variant detection by sequencing, genomic profiling, expression profiling, and/or the like. Non-limiting examples of genes of interest which may be amplified according to the methods of the present disclosure include one, each, or any combination of the genes provided in FIG. 3.

In certain aspects, a panel of amplification primers is employed, and the panel is adapted, in addition to amplifying one or more copy number stable genes, to amplify two or more regions of interest present in genomic DNA, including but not limited to, "hot spot" regions that are frequently mutated in human cancer genes. Such a panel may be specifically designed by one practicing the subject methods, or the practitioner may order one of the various commercially available panels, such as an Ion AmpliSeq™ Cancer Hotspot Panel available from Life Technologies, Inc. (Carlsbad, Calif.).

The one or more amplification primers may be designed to be sufficiently complementary to their corresponding target nucleic acids in the nucleic acid sample, such that the primer specifically hybridizes to its target under hybridization conditions.

The term "complementary" as used herein refers to a nucleotide sequence that base-pairs by non-covalent bonds to a region of the copy number stable gene or nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, the amplification primer may be perfectly (i.e., 100%) complementary to the copy number stable gene, or the primer and the copy number stable gene may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

As used herein, the term "hybridization conditions" means conditions in which a primer specifically hybridizes to a region of a copy number stable gene or nucleic acid of interest. Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The $T_m$ of a duplex may be experimentally determined or predicted using the following formula $T_m=81.5+16.6(\log_{10}[Na^+])+0.41$ (fraction G+C)−(60/N), where N is the chain length and [Na$^+$] is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict $T_m$ of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

The nucleic acid sequences present in the genomes, transcriptomes, etc. of nucleic acid sources of interest are readily available from resources such as the nucleic acid sequence databases of the National Center for Biotechnology Information (NCBI), the European Molecular Biology Laboratory-European Bioinformatics Institute (EMBL-EBI), and the like. Based on such sequence information, one can design/select one or more amplification primers to amplify the one or more copy number stable genes, and optionally, one or more nucleic acids of interest.

In certain aspects, the one or more amplification primers include a sequencing adapter (e.g., 5' relative to a 3' hybridization region of the primer(s)). By "sequencing adapter" is meant one or more nucleic acid domains that include at least a portion of a nucleic acid sequence (or complement thereof) utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, the one or more amplification primers include a sequencing adapter that includes a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a barcode domain (e.g., a domain that uniquely identifies the sample source of the nucleic acid being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same sequencing adapter.

The one or more amplification primers may include a sequencing adapter of any length and sequence suitable for the sequencing platform of interest. In certain aspects, the nucleic acid domains are from 4 to 100 nucleotides in length, such as from 6 to 75, from 8 to 50, or from 10 to 40 nucleotides in length.

The one or more amplification primers may include one or more nucleotides (or analogs thereof) that are modified or otherwise non-naturally occurring. For example, the amplification primers may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the primers and/or resulting amplicons.

Nucleic Acid Samples

The nucleic acid sample may be any nucleic acid sample that includes, or is suspected of including, one or more copy number stable genes, and optionally, one or more nucleic acids of interest, e.g., one or more nucleic acids in addition to the one or more copy number stable genes for which amplification is desirable. Amplification of one or more copy number stable genes and one or more nucleic acids of interest may be desirable for a variety of reasons, including but not limited to, sequencing the amplification products (or "amplicons") of the one or more copy number stable genes and one or more nucleic acids of interest. Sequencing the amplicons enables one to determine the nucleotide sequence(s) of—and number of sequencing runs corresponding to—the one or more copy number stable genes and one or more nucleic acids of interest, which may in turn be used to determine the copy number of one or more of the nucleic acids of interest as described in detail below. In certain aspects, determining the copy number of one or more of the nucleic acids of interest enables one to determine whether copy number variation (CNV) exists for one or more of the one or more nucleic acids of interest in the sample.

The nucleic acid sample may be one or more cells of interest, or a nucleic acid sample isolated from one or more cells of a cellular sample of interest. For example, the nucleic acid sample may be a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of a mammal (e.g., a human, a rodent (e.g., a mouse), or any other mammal of interest). In other aspects, the nucleic acid sample is isolated from a source other than a mammal, such as bacteria, yeast, insects (e.g., drosophila), amphibians (e.g., frogs (e.g., Xenopus)), viruses, plants, or any other non-mammalian nucleic acid sample source.

According to certain embodiments, the nucleic acid sample is isolated from a biological sample, such as a biological fluid or a biological tissue. Examples of biological fluids include urine, blood, plasma, serum, saliva, semen, stool, sputum, cerebral spinal fluid, tears, mucus, sperm, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cells.

According to certain embodiments, the nucleic acid sample is a tumor nucleic acid sample (that is, a nucleic acid sample isolated from a tumor). "Tumor", as used herein, refers to all neoplastic cell growth and proliferation, whether malignant or benign, and all pre-cancerous and cancerous cells and tissues. The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, and the like. In certain aspects, the nucleic acid sample includes nucleic acids from one or more circulating tumor cells (CTCs).

According to certain embodiments, the nucleic acid sample is a deoxyribonucleic acid (DNA) sample. DNA samples of interest include, but are not limited to, genomic DNA samples, mitochondrial DNA samples, complementary DNA (cDNA, synthesized from any RNA or DNA of interest) samples, recombinant DNA samples (e.g., plasmid DNA samples), and any other DNA samples of interest.

In certain aspects, the nucleic acid sample is a ribonucleic acid (RNA) sample. RNA samples of interest include, but are not limited to, messenger RNA (mRNA) samples, small/short interfering RNA (siRNA) samples, microRNA (miRNA) samples, any other DNA samples of interest.

Approaches, reagents and kits for isolating DNA and RNA from sources of interest are known in the art and commercially available. For example, kits for isolating DNA from a source of interest include the DNeasy®, RNeasy®, QIAamp®, QIAprep® and QIAquick® nucleic acid isolation/purification kits by Qiagen, Inc. (Germantown, Mdd); the DNAzol®, ChargeSwitch®, Purelink®, and Gen-eCatcher® nucleic acid isolation/purification kits by Life Technologies, Inc. (Carlsbad, Calif.); the NucleoMag®, NucleoSpin®, and NucleoBond® nucleic acid isolation/purification kits by Clontech Laboratories, Inc. (Mountain View, Calif.). In certain aspects, the nucleic acid is isolated from a fixed biological sample, e.g., formalin-fixed, paraffin-embedded (FFPE) tissue. Genomic DNA and RNA from FFPE tissue may be isolated using commercially available kits—such as the AllPrep® DNA/RNA FFPE kit by Qiagen, Inc. (Germantown, Md.), the RecoverAll® Total Nucleic Acid Isolation kit for FFPE by Life Technologies, Inc. (Carlsbad, Calif.), and the NucleoSpin® FFPE kits by Clontech Laboratories, Inc. (Mountain View, Calif.).

When it is desirable to control the size of the nucleic acids in the nucleic acid sample, the sample may be subjected to shearing/fragmentation, e.g., to generate nucleic acids that are shorter in length as compared to precursor non-sheared nucleic acids (e.g., genomic DNA) in the original sample. Suitable shearing/fragmentation strategies include, but are not limited to, passing the sample one or more times through a micropipette tip or fine-gauge needle, nebulizing the sample, sonicating the sample (e.g., using a focused-ultrasonicator by Covaris, Inc. (Woburn, Mass.)), bead-mediated shearing, enzymatic shearing (e.g., using one or more DNA-shearing e.g., restriction, enzymes), chemical based fragmentation, e.g., using divalent cations, fragmentation buffer (which may be used in combination with heat) or any other suitable approach for shearing/fragmenting precursor nucleic acids to generate a shorter nucleic acids. In certain aspects, the nucleic acids generated by shearing/fragmentation of a starting nucleic acid sample has a length of from 50 to 10,000 nucleotides, from 100 to 5000 nucleotides, from 150 to 2500 nucleotides, from 200 to 1000 nucleotides, e.g., from 250 to 500 nucleotides in length. According to certain embodiments, the nucleic acids generated by shearing/fragmentation of a starting nucleic acid sample has a length of from 10 to 20 nucleotides, from 20 to 30 nucleotides, from 30 to 40 nucleotides, from 40 to 50 nucleotides, from 50 to 60 nucleotides, from 60 to 70 nucleotides, from 70 to 80 nucleotides, from 80 to 90 nucleotides, from 90 to 100 nucleotides, from 100 to 150 nucleotides, from 150 to 200, from 200 to 250 nucleotides in length, or from 200 to 1000 nucleotides or even from 1000 to 10,000 nucleotides, for example, as appropriate for a sequencing platform in which one desires to sequence amplicons produced upon amplification of the one or more copy number stable genes and any other amplicons that may be present, e.g., amplicons produced from nucleic acids of interest present in the nucleic acid sample.

Reaction Conditions

As summarized above, the nucleic acid sample and the one or more amplification primers adapted to amplify a region of one or more copy number stable genes are combined in a reaction mixture under conditions sufficient to amplify the one or more copy number stable genes. By "conditions sufficient to amplify the one or more copy number stable genes" is meant reaction conditions that permit polymerase-mediated extension of a 3' end of the one or more amplification primers. Achieving suitable reaction conditions may include selecting reaction mixture components, concentrations thereof, and a reaction temperature to create an environment in which a polymerase is active and the relevant nucleic acids in the reaction interact (e.g., hybridize) with one another in the desired manner. Suitable hybridization conditions are described in detail above.

In addition to the nucleic acid sample, the one or more amplification primers, a polymerase, and dNTPs, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction to occur. Other components may be included, such as one or more nuclease inhibitors (e.g., a DNase inhibitor and/or an RNase inhibitor), one or more additives for facilitating amplification/replication of GC rich sequences, one or more enzyme-stabilizing components (e.g., DTT present at a final concentration ranging from 1 to 10 mM (e.g., 5 mM)), and/or any other reaction mixture components useful for facilitating polymerase-mediated extension reactions.

The reaction mixture can have a pH suitable for the primer extension reaction. In certain embodiments, the pH of the reaction mixture ranges from 5 to 9, such as from 7 to 9. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for amplification may vary according to factors such as the particular polymerase employed, the melting temperatures of the one or more amplification primers employed, etc. According to certain embodiments, the reaction mixture conditions include bringing the reaction mixture to a temperature ranging from 4° C. to 80° C., such as from 16° C. to 75° C., e.g., from 37° C. to 72° C.

Example Additional Embodiments

The methods of the present disclosure may include one or more steps in addition to the combining step described above. For example, the methods may further include utilizing the amplified one or more copy number stable genes (and any other amplicons that may be present) in a downstream application/assay of interest. The amplified nucleic acids may be utilized directly (optionally after a purification step), or may be modified prior to being utilized in a downstream application/assay of interest.

In certain aspects, it may be desirable to sequence the amplification products (e.g., using a Sanger sequencing system, a next generation sequencing (NGS) system, or the like), where the addition of one or more sequencing adapters to the amplification products is useful or necessary for sequencing on a particular sequencing system of interest. Accordingly, in certain aspects, the methods further include adding a sequencing adapter to the amplified one or more copy number stable genes and any other amplicons that may be present. Such a step may be performed whether or not the amplicons already include one or more sequencing adapters (e.g., by virtue of the one or more amplification primers including one or more sequencing adapters as described above). Sequencing adapters that may be added include, e.g., one or more capture domains, one or more sequencing primer binding domains, one or more barcode domains, one or more barcode sequencing primer binding domains, one or more molecular identification domains, a complement of any such domains, or any combination thereof. Further details regarding sequencing adapters are described hereinabove.

According to certain embodiments, the methods include sequencing the amplified one or more copy number stable genes, and any other amplicons produced during the combining step, e.g., amplicons produced from one or more nucleic acids of interest as described above. Such amplification products may be sequenced directly (optionally after a purification step), or may be modified prior to being sequenced. Modifications prior to sequencing include, but are not limited to, the addition of one or more sequencing adapters as described above, and/or any other useful modifications for sequencing the amplicons on a sequencing platform of interest.

The sequencing may be carried out on any suitable sequencing platform, including a Sanger sequencing platform, a next generation sequencing (NGS) platform (e.g., using a next generation sequencing protocol), or the like. NGS sequencing platforms of interest include, but are not limited to, a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest. Detailed protocols for preparing the amplicons for sequencing (e.g., by further amplification (e.g., solid-phase amplification), or the like), sequencing the amplicons, and analyzing the sequencing data are available from the manufacturer of the sequencing system of interest.

In certain aspects, the methods further include determining the copy number of the one or more nucleic acids of interest present in the nucleic acid sample (e.g., the copy number of a nucleic acid of interest present in a genome from which the nucleic acid sample is derived. Such a determination may be based on, e.g., the number of sequencing reads corresponding to the one or more nucleic acids of interest present in the nucleic acid sample, and the number of sequencing reads corresponding to the one or more copy number stable genes.

According to some embodiments, determining the copy number of the one or more nucleic acids of interest present in the nucleic acid sample includes determining a ratio of the number of sequencing reads corresponding to the one or more nucleic acids of interest present in the nucleic acid sample to the number of sequencing reads corresponding to the one or more copy number stable genes. Determining the copy number of the one or more nucleic acids of interest present in the nucleic acid sample may be based on a ratio.

According to some embodiments, the following formula is used to determine the copy number of a nucleic acid of interest present in a genome from which the nucleic acid sample is derived:

$$c\_NA/c\_CNSG = r\_NA/r\_CNSG \qquad \text{(Formula I)}$$

where c=the copy number, r=the number of sequencing reads, NA=the nucleic acid of interest, and CNSG=the copy number stable gene.

Utility

The methods of the present disclosure (as well as the compositions, nucleic acids sequencing systems and kits described below) find use in a variety of applications, including but not limited to, applications in which it is desirable to determine the copy number of one or more genomic regions (e.g., genes, intergenic regions, etc.) present in a source of nucleic acids (e.g., cells or tissues of interest, such as tumor cells or tissues of interest). Applications of interest include, e.g., research applications, clinical applications (e.g., clinical diagnostic applications), etc., and the methods may be employed in such applications to assess whether, e.g., a cell or tissue exhibits copy number variation (CNV) in one or more genomic regions of interest. The methods also find use in determining the nucleotide sequences of nucleic acids amplified from the nucleic acid sample and/or quantifying the amount of the one or more nucleic acids of interest present in the sample.

Current CNV detection workflows using amplicon-based NGS relies upon inclusion of control samples in every run achieved through use of matched pairs (e.g., matched tumor/normal pairs) or a representative pooled normal sample. These controls are used to correct for coverage bias of amplicons, an artifact of the use of PCR to amplify, e.g., cancer panel targets. Sequencing platform manufacturers such as Ion Torrent® also recommend additional guidelines for successful CNV detection, such as having <20% of all amplicons in a panel impacted to copy number changes and having >10 amplicons covering a region harboring a copy number alteration, placing constraints upon panel design.

The methods of the present disclosure—which involve the amplification of one or more copy number stable genes—provide advantages over existing approaches in a number of respects. For example, in certain embodiments, the methods of the present disclosure are advantageous in the context of nucleic acid sequencing for reasons including, but not limited to, the presence of internal control standards in sequencing libraries generated using the methods of the present disclosure, which internal control standards enable sample normalization and accurate copy number determination. The internal control standards are the amplicons produced from the one or more copy number stable genes using the method of the present disclosure.

When the methods of the present disclosure are used to prepare a sequencing library, the amplicons produced from the one or more copy number stable genes may be used to normalize sequencing reads so that copy number information may be derived from sequencing data, obviating the need for matched samples (e.g., matched tumor/normal samples), pooled normal controls, universal control standards, and/or the like. Reliance upon external control samples during NGS sequencing reduces sample throughput, e.g., the number of patient samples that can be analyzed in a given sequencing run. The provision of internal copy number controls as provided by embodiments of the present disclosure, therefore, increases sample throughput relative to current approaches. In addition, matched patient normal sample availability may be limited, rendering copy number determination impracticable if a pooled normal sample is not routinely used and/or available. Moreover, use of pooled normal samples to normalize NGS reads may lead to erroneous copy number results if an abnormal copy number is present within the pool. Such issues are precluded according to embodiments of the subject methods.

In certain aspects, the methods provide sequencing read normalization required for NGS sequencing Copy Number Variation (CNV) determination that is built into each sample's sequencing library preparation reaction, obviating the requirement for additional control samples, each control sample requiring a separate library preparation reaction, sequencing run, etc.

Compositions

Aspects of the present disclosure further include compositions. The compositions of the present disclosure find a variety of uses, including in some aspects, practicing the methods of the present disclosure.

According to certain embodiments, provided is a composition that includes a nucleic acid sample and one or more amplification primers adapted to amplify a region of one or more copy number stable genes. The composition may include any nucleic acid sample of interest and any suitable amplification primer(s), including any of the nucleic acid samples and amplification primers described above in the section relating to the methods of the present disclosure.

In certain aspects, the composition includes one or more amplification primers adapted to amplify one or more nucleic acids of interest present in the nucleic acid sample, in addition to the one or more amplification primers adapted to amplify a region of one or more copy number stable genes. For example, the composition may include a pool (or "panel") of primers for amplification of one or more nucleic acids of interest and one or more copy number stable genes. Panels of interest include, but are not limited to, sequencing panels adapted to amplify one or more genomic regions (e.g., genes) of interest in a tissue of interest (e.g., tumor tissue) and one or more copy number stable genes. Downstream sequencing of the copy number stable genes enables, e.g., determination of copy number and any variation thereof in the one or more genomic regions of interest.

Other components which may be present in the compositions of the present disclosure include, but are not limited to, a polymerase, dNTPs, a buffer component that establishes an appropriate pH, a salt (e.g., e.g., NaCl, KCl, or the like), a metal cofactor (e.g., $Mg^{2+}$, $Mn^{2+}$, or the like), a nuclease inhibitor (e.g., a DNase inhibitor and/or an RNase inhibitor), an additive for facilitating amplification/replication of GC rich sequences, an enzyme-stabilizing component (e.g., DTT), any other reaction mixture components (e.g., useful for facilitating polymerase-mediated extension reactions), a known amount of internal standard nucleic acids corresponding to one or more copy number stable genes, and any combination thereof.

In certain aspects, a composition of the present disclosure includes the amplicons produced by the methods of the present disclosure. According to certain embodiments, such compositions include the amplicons in purified form (e.g., substantially or completely separated from the amplification reaction mixture components). The amplicons may include a sequencing adapter provided during or after the amplification reaction as described above.

Any of the compositions of the present disclosure may be present in a container. Suitable containers include, but are not limited to, tubes, vials, plates (e.g., a 96- or other-well plate).

Any of the compositions of the present disclosure may be present in a device. Devices of interest include, but are not limited to, an incubator, a thermocycler, a sequencing system (e.g., a Sanger sequencing system or a next generation sequencing system), a microfluidic device, or the like.

Nucleic Acid Sequencing Systems

Also provided by the present disclosure are nucleic acid sequencing systems. According to certain embodiments, the nucleic acid sequencing systems find use in sequencing amplicons generated using the methods of the present disclosure.

In certain aspects, a sequencing system of the present disclosure includes a collection of nucleic acids. The collection of nucleic acids includes amplicons corresponding to nucleic acids of interest present in a nucleic acid sample, and amplicons corresponding to one or more copy number stable genes present in the nucleic acid sample.

According to certain embodiments, the sequencing system includes amplicons generated from any of the one or more amplification primers adapted to amplify a region of one or more copy number stable genes and any of the one or more amplification primers adapted to amplify one or more nucleic acids of interest as described above in the section relating to the methods of the present disclosure.

The amplicons may include a sequencing adapter provided during the amplification reaction that produced the amplicons (e.g., provided according to embodiments of the subject methods) and/or after the amplification reaction (e.g., provided according to embodiments of the subject methods).

The sequencing system may be any sequencing system of interest, including a Sanger sequencing system, a next generation sequencing (NGS) system, or the like. In certain aspects the sequencing system is an NGS system. NGS systems of interest include, but are not limited to, a sequencing system provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems), or any other suitable NGS systems.

The collection of nucleic acids may be present in a component of the sequencing system. By way of example, the collection of nucleic acids may be present in a sample preparation component of the sequencing system, e.g., a component of the sequencing system where nucleic acids of the collection are fragmented and/or sequencing adapters are added to the nucleic acids of the collection. Also by way of example, the collection of nucleic acids may be present in a solid-phase amplification component of the sequencing system, where solid-phase amplification of the nucleic acids of the collection may occur. An example of such a solid-phase amplification component of a sequencing system is the flow cell of Illumina-based sequencing systems, where cluster generation occurs. Another example of such a solid-phase amplification component of a sequencing system is the Ion OneTouch™ 2 component for producing templates suitable for sequencing on an Ion PGM™ system, Ion Proton™ system, or other NGS system provided by Ion Torrent™. The collection of nucleic acids may be present in any component of a sequencing system useful for utilizing the collection of nucleic acids to obtain the nucleic acid sequences thereof.

According to certain embodiments, the sequencing system is adapted to determine the copy number of the nucleic acids of interest present in the nucleic acid sample. In certain aspects, the determination is based on the number of sequencing reads corresponding to nucleic acids of interest in the nucleic acid sample, and the number of sequencing reads corresponding to the one or more copy number stable genes. In certain aspects, such a sequencing system is adapted to determine a ratio of the number of sequencing reads corresponding to nucleic acids of interest in the nucleic acid sample to the number of sequencing reads corresponding to the one or more copy number stable genes. When the sequencing system is adapted to determine such a ratio, the system may be further adapted to determine the copy number of the nucleic acids of interest present in the nucleic acid sample based on the ratio of the number of sequencing reads corresponding to nucleic acids of interest in the nucleic acid sample to the number of sequencing reads corresponding to the one or more copy number stable genes.

By "adapted to determine the copy number of the nucleic acids of interest present in the nucleic acid sample," "adapted to determine the copy number of the nucleic acids of interest present in the nucleic acid sample based on a ratio of the number of sequencing reads corresponding to nucleic acids of interest in the nucleic acid sample to the number of sequencing reads corresponding to the one or more copy number stable genes," and the like, is meant that the sequencing system includes the components and functionality to perform the recited determinations. For example, in certain aspects, the sequencing system includes a processor and a computer-readable medium (e.g., a non-transitory computer-readable medium). The computer-readable medium includes instructions executable by the processor to, e.g., determine the copy number of the nucleic acids of interest present in the nucleic acid sample as described above, determine a ratio of the number of sequencing reads corresponding to nucleic acids of interest in the nucleic acid sample to the number of sequencing reads corresponding to the one or more copy number stable genes, and/or the like. Example formulas/algorithms which may be implemented by the sequencing systems of the present disclosure are described above in the section relating to the methods of the present disclosure.

Kits

As summarized above, the present disclosure provides kits. According to certain embodiments, the kits include one or more amplification primers adapted to amplify a region of one or more copy number stable genes present in a nucleic acid sample of interest, and a container (e.g., a tube). In certain aspects, the one or more amplification primers are present in the container.

The subject kits may include any of the amplification primers adapted to amplify any of the copy number stable genes described above in relation to the methods of the present disclosure.

In certain aspects, the kits include one or more amplification primers adapted to amplify one or more nucleic acids of interest present in the nucleic acid sample, in addition to the one or more amplification primers adapted to amplify a region of one or more copy number stable genes. For example, a kit of the present disclosure may include a pool (or "panel") of primers for amplification of one or more nucleic acids of interest and one or more copy number stable genes. Panels of interest include, but are not limited to, sequencing panels adapted to amplify one or more genomic regions (e.g., genes) of interest in a tissue of interest (e.g., tumor tissue) and one or more copy number stable genes. Downstream sequencing of the copy number stable genes enables, e.g., determination of copy number and any variation thereof in the one or more genomic regions of interest.

According to certain embodiments, the kits include one or more of a polymerase, dNTPs, a buffer component that establishes an appropriate pH, a salt (e.g., e.g., NaCl, KCl, or the like), a metal cofactor (e.g., $Mg^{2+}$, $Mn^{2+}$, or the like), a nuclease inhibitor (e.g., a DNase inhibitor and/or an RNase inhibitor), an additive for facilitating amplification/replication of GC rich sequences, an enzyme-stabilizing component (e.g., DTT), internal standard nucleic acids corresponding to one or more copy number stable genes, and/or any other reaction mixture components, e.g., useful for facilitating polymerase-mediated extension reactions.

Components of the subject kits may be present in separate containers, or multiple components may be present in a single container. For example, when two or more amplification primers are included in the kit, each of the two or more amplification primers may be present in separate containers, subsets of the two or more amplification primers may be present in separate containers, each of the two or more amplification primers may be present in a single container, etc.

The one or more amplification primers may be provided in any suitable container. For example, the amplification primers may be provided in a single tube (e.g., vial), in one or more wells of a plate (e.g., a 96-well plate, a 384-well plate, etc.), or the like.

In addition to the above-mentioned components, a kit of the present disclosure may further include instructions for using the components of the kit, e.g., to practice the methods of the present disclosure. For example, the kit may include instructions for using the one or more amplification primers adapted to amplify a region of one or more copy number stable genes to determine the copy number of one or more genes of interest present in the nucleic acid sample of interest. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following examples are offered by way of illustration and not by way of limitation.

EXPERIMENTAL

Example 1: Inclusion of Primers Adapted to Amplify Copy Number Stable Genes in a Sequencing Panel In this example, amplification primers adapted to amplify 10 genes identified based upon their proximity to ohnologs were included in a sequencing panel for sequencing library preparation. Ohnologs and genes in close proximity to ohnologs have fewer copy number alterations than genes further away from ohnolog-rich regions. See, e.g., Makino et al. (2013) *Nature Communications* 4:2283. These ten additional genes were included in a custom TumorSeq DNA Panel and served as internal controls for CNV detection. The ten genes included in the panel for the purposes of internal control standards were: HNRNPR (Entrez Gene ID 10236), TCEB3 (Entrez Gene ID 6924), IL22RA1 (Entrez Gene ID 58985), RCAN3 (Entrez Gene ID 11123), GJB5 (Entrez Gene ID 2707), SLC25A44 (Entrez Gene ID 9673), MT3 (Entrez Gene ID 4504), MT1X (Entrez Gene ID 4501), NUP93 (Entrez Gene ID 9688) and RABL2B (Entrez Gene ID 11158). Sequencing data was collected using a custom NGS panel that included these ten genes. Data for these ten genes is shown in FIG. 1.

The ten genes identified to serve as internal controls were identified using both the reference mentioned and bioinformatics tools, using the following method: (1) regions on chromosomes lacking ClinVar and DGV entries for CNV were located using bioinformatics tools; (2) coordinates from supplementary Table 1 of Makino et al. (supra) were updated to reflect the current build of the human genome (hg19), using bioinformatics tools; (3) CNV-free regions identified in step (1) were cross-referenced with the table from step (2); (4) genes closest to ohnologs were identified; and (5) CNV status was confirmed using DGV (Database of Genomic Variation) entry data from Gene Cards. Copy number stable genes in the human genome identified using this approach are graphically illustrated in FIG. 2.

Notwithstanding the appended clauses, the disclosure set forth herein is also defined by the following clauses:

1. A method of amplifying nucleic acids, comprising: combining:
    a nucleic acid sample; and
    one or more amplification primers adapted to amplify a region of one or more copy number stable genes, in a reaction mixture under conditions sufficient to amplify the one or more copy number stable genes.
2. The method according to Clause 1, wherein the one or more amplification primers are adapted to amplify one or more copy number stable genes located in ohnolog-rich regions of a genome.
3. The method according to Clause 2, wherein the ohnolog-rich regions of the genome are regions comprising a proportion of ohnologs greater than 50% in a 2 Mb window.
4. The method according to Clause 2 or Clause 3, wherein the one or more amplification primers are adapted to amplify one or more ohnologs.
5. The method according to Clause 2, wherein the one or more amplification primers are adapted to amplify a region of one or more copy number stable genes selected from the group consisting of: HNRNPR, TCEB3, IL22RA1, RCAN3, GJB5, SLC25A44, MT3, MT1X, NUP93, RABL2B, and combinations thereof.
6. The method according to Clause 5, wherein the one or more amplification primers are adapted to amplify a region of each of the copy number stable genes HNRNPR, TCEB3, IL22RA1, RCAN3, GJB5, SLC25A44, MT3, MT1X, NUP93, and RABL2B.
7. The method according to any one of Clauses 1 to 6, wherein the combining comprises combining a known amount of nucleic acids corresponding to one or more copy number stable genes with the nucleic acid sample and the one or more amplification primers adapted to amplify a region of one or more copy number stable genes.
8. The method according to any one of Clauses 1 to 7, wherein the nucleic acid sample comprises nucleic acids isolated from one or more cells of a cellular sample of interest.
9. The method according to Clause 8, wherein the cellular sample of interest is a single cell.
10. The method according to Clause 8 or Clause 9 wherein the cellular sample of interest is a tumor sample.
11. The method according to any one of Clauses 1 to 10, wherein the one or more amplification primers comprise a sequencing adapter.
12. The method according to any one of Clauses 1 to 11, wherein the one or more amplification primers are non-random primers.
13. The method according to any one of Clauses 1 to 12, further comprising adding a sequencing adapter to the amplified one or more copy number stable genes.
14. The method according to any one of Clauses 1 to 13, further comprising amplifying one or more nucleic acids of interest present in the nucleic acid sample.
15. The method according to Clause 14, further comprising sequencing the amplified one or more copy number stable genes and the amplified one or more nucleic acids of interest.
16. The method according to Clause 15, wherein the sequencing is by a next generation sequencing protocol.
17. The method according to Clause 15 or Clause 16, further comprising determining the copy number of the one or more nucleic acids of interest present in the nucleic acid sample based on:
    the number of sequencing reads corresponding to the one or more nucleic acids of interest present in the nucleic acid sample; and
    the number of sequencing reads corresponding to the one or more copy number stable genes.
18. The method according to Clause 17, wherein determining the copy number of the one or more nucleic acids of interest present in the nucleic acid sample is based on a ratio of the number of sequencing reads corresponding to the one or more nucleic acids of interest present in the nucleic acid sample to the number of sequencing reads corresponding to the one or more copy number stable genes.
19. A composition, comprising:
    a nucleic acid sample; and
    one or more amplification primers adapted to amplify a region of one or more copy number stable genes.
20. The composition according to Clause 19, wherein the one or more amplification primers are adapted to amplify one or more copy number stable genes located in ohnolog-rich regions of a genome.

21. The composition according to Clause 20, wherein the ohnolog-rich regions of the genome are regions comprising a proportion of ohnologs greater than 50% in a 2 Mb window.
22. The composition according to any one of Clauses 19 to 21, wherein the one or more amplification primers are adapted to amplify one or more ohnologs.
23. The composition according to Clause 20, wherein the one or more amplification primers are adapted to amplify a region of one or more copy number stable genes selected from the group consisting of: HNRNPR, TCEB3, IL22RA1, RCAN3, GJB5, SLC25A44, MT3, MT1X, NUP93, RABL2B, and combinations thereof.
24. The composition according to Clause 23, wherein the one or more amplification primers are adapted to amplify a region of each of the copy number stable genes HNRNPR, TCEB3, IL22RA1, RCAN3, GJB5, SLC25A44, MT3, MT1X, NUP93, and RABL2B.
25. The composition according to any one of Clauses 19 to 24, further comprising a known amount of internal standard nucleic acids corresponding to one or more copy number stable genes.
26. The composition according to any one of Clauses 19 to 24, wherein the nucleic acid sample comprises nucleic acids isolated from one or more cells of a cellular sample of interest.
27. The composition according to Clause 26, wherein the cellular sample of interest is a single cell.
28. The composition according to Clause 26 or Clause 27, wherein the cellular sample of interest is a tumor sample.
29. The composition according to any one of Clauses 19 to 28, wherein the one or more amplification primers comprise a sequencing adapter.
30. The composition according to any one of Clauses 19 to 29, wherein the one or more amplification primers are non-random primers.
31. A nucleic acid sequencing system, comprising:
    a collection of nucleic acids comprising: amplicons corresponding to nucleic acids of interest present in a nucleic acid sample; and amplicons corresponding to one or more copy number stable genes.
32. The sequencing system according to Clause 31, wherein the one or more copy number stable genes are located in ohnolog-rich regions of a genome.
33. The sequencing system according to Clause 32, wherein the ohnolog-rich regions of the genome are regions comprising a proportion of ohnologs greater than 50% in a 2 Mb window.
34. The sequencing system according to Clause 31, wherein the one or more copy number stable genes are one or more ohnologs.
35. The sequencing system according to Clause 31, wherein the one or more copy number stable genes are selected from the group consisting of: HNRNPR, TCEB3, IL22RA1, RCAN3, GJB5, SLC25A44, MT3, MT1X, NUP93, RABL2B, and combinations thereof.
36. The sequencing system according to Clause 35, wherein the one or more copy number stable genes are each of HNRNPR, TCEB3, IL22RA1, RCAN3, GJB5, SLC25A44, MT3, MT1X, NUP93, and RABL2B.
37. The sequencing system according to any one of Clauses 31 to 36, wherein the collection of nucleic acids further comprises amplicons corresponding to a known amount of internal standard nucleic acids corresponding to one or more copy number stable genes.
38. The sequencing system according to any one of Clauses 31 to 36, wherein the nucleic acid sample comprises nucleic acids isolated from one or more cells of a cellular sample of interest.
39. The sequencing system according to Clause 38, wherein the cellular sample of interest is a single cell.
40. The sequencing system according to Clause 38 or Clause 39, wherein the cellular sample of interest is a tumor sample.
41. The sequencing system according to any one of Clauses 31 to 40, wherein the amplicons were amplified using non-random primers.
42. The sequencing system according to any one of Clauses 31 to 41, wherein the sequencing system is adapted to determine the copy number of the nucleic acids of interest present in the nucleic acid sample based on: the number of sequencing reads corresponding to nucleic acids of interest in the nucleic acid sample; and the number of sequencing reads corresponding to the one or more copy number stable genes.
43. The sequencing system according to Clause 42, wherein the sequencing system is adapted to determine the copy number of the nucleic acids of interest present in the nucleic acid sample based on a ratio of the number of sequencing reads corresponding to nucleic acids of interest in the nucleic acid sample to the number of sequencing reads corresponding to the one or more copy number stable genes.
44. The sequencing system according to any one of Clauses 31 to 43, wherein the sequencing system is a next generation sequencing system.
45. A kit comprising:
    one or more amplification primers adapted to amplify a region of one or more copy number stable genes present in a nucleic acid sample of interest; and
    a container.
46. The kit according to Clause 45, wherein the one or more amplification primers are adapted to amplify one or more copy number stable genes located in ohnolog-rich regions of a genome.
47. The kit according to Clause 46, wherein the ohnolog-rich regions of the genome are regions comprising a proportion of ohnologs greater than 50% in a 2 Mb window.
48. The kit according to any one of Clauses 45 to 47, wherein the one or more amplification primers are adapted to amplify one or more ohnologs.
49. The kit according to Clause 46, wherein the one or more amplification primers are adapted to amplify a region of one or more copy number stable genes selected from the group consisting of: HNRNPR, TCEB3, IL22RA1, RCAN3, GJB5, SLC25A44, MT3, MT1X, NUP93, RABL2B, and combinations thereof.
50. The kit according to Clause 49, wherein the one or more amplification primers are adapted to amplify a region of each of the copy number stable genes HNRNPR, TCEB3, IL22RA1, RCAN3, GJB5, SLC25A44, MT3, MT1X, NUP93, and RABL2B.
51. The kit according to any one of Clauses 45 to 50, further comprising internal standard nucleic acids corresponding to one or more copy number stable genes.
52. The kit according to any one of Clauses 45 to 50, wherein the nucleic acid sample comprises nucleic acids isolated from one or more cells of a cellular sample of interest.
53. The kit according to Clause 52, wherein the cellular sample of interest is a single cell.

54. The kit according to Clause 52 or Clause 53, wherein the cellular sample of interest is a tumor sample.
55. The kit according to any one of Clauses 45 to 54, wherein the one or more amplification primers comprise a sequencing adapter.
56. The kit according to any one of Clauses 45 to 55, wherein the one or more amplification primers are non-random primers.
57. The kit according to any one of Clauses 45 to 56, further comprising instructions for using the one or more amplification primers adapted to amplify a region of one or more copy number stable genes to determine the copy number of one or more genes of interest present in the nucleic acid sample of interest.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:
1. A method of amplifying nucleic acids, comprising:
combining:
a nucleic acid sample; and
amplification primers adapted to amplify a region of six or more copy number stable genes selected from a group consisting of: HNRNPR, TCEB3, IL22RA1, RCAN3, GJB5, SLC25A44, MT3, MT1X, NUP93, RABL2B,
in a reaction mixture under conditions sufficient to amplify the six or more copy number stable genes.
2. The method according to claim 1, further comprising amplifying one or more nucleic acids of interest present in the nucleic acid sample.
3. The method according to claim 2, further comprising sequencing the amplified one or more copy number stable genes and the amplified one or more nucleic acids of interest.
4. The method according to claim 3, further comprising determining the copy number of the one or more nucleic acids of interest present in the nucleic acid sample based on:
the number of sequencing reads corresponding to the one or more nucleic acids of interest present in the nucleic acid sample; and
the number of sequencing reads corresponding to the one or more copy number stable genes.
5. The method according to claim 1, wherein the amplification primers are adapted to amplify a region of 8 or more copy number stable genes selected from the group consisting of: HNRNPR, TCEB3, IL22RA1, RCAN3, GJB5, SLC25A44, MT3, MT1X, NUP93, and RABL2.
6. The method according to claim 1, wherein the amplification primers are adapted to amplify a region of each of the copy number stable genes selected from the group consisting of: HNRNPR, TCEB3, IL22RA1, RCAN3, GJB5, SLC25A44, MT3, MT1X, NUP93, and RABL2B.
7. A method of amplifying nucleic acids, comprising:
combining:
a nucleic acid sample; and
primers adapted to amplify a region of each of the copy number stable genes selected from the group consisting of: SLC25A44, MT3, MT1X, NUP93, and RABL2B.
8. The method according to claim 1, wherein the combining comprises combining a known amount of nucleic acids corresponding to six or more copy number stable genes with the nucleic acid sample and the amplification primers adapted to amplify a region of six or more copy number stable genes.
9. The method according to claim 1, wherein the nucleic acid sample comprises nucleic acids isolated from one or more cells of a cellular sample of interest.
10. The method according to claim 9, wherein the cellular sample of interest is a single cell.
11. The method according to claim 9, wherein the cellular sample of interest is a tumor sample.
12. The method according to claim 4, wherein determining the copy number of the one or more nucleic acids of interest present in the nucleic acid sample is based on a ratio of the number of sequencing reads corresponding to the one or more nucleic acids of interest present in the nucleic acid sample to the number of sequencing reads corresponding to the one or more copy number stable genes.
13. The method according to claim 7, further comprising amplifying one or more nucleic acids of interest present in the nucleic acid sample.
14. The method according to claim 13, further comprising sequencing the amplified one or more copy number stable genes and the amplified one or more nucleic acids of interest.
15. The method according to claim 14, further comprising determining the copy number of the one or more nucleic acids of interest present in the nucleic acid sample based on:
the number of sequencing reads corresponding to the one or more nucleic acids of interest present in the nucleic acid sample; and
the number of sequencing reads corresponding to the one or more copy number stable genes.
16. The method according to claim 7, wherein the combining comprises combining a known amount of nucleic acids corresponding to the copy number stable genes with the nucleic acid sample and the amplification primers adapted to amplify a region of the copy number stable genes.
17. The method according to claim 7, wherein the nucleic acid sample comprises nucleic acids isolated from one or more cells of a cellular sample of interest.
18. The method according to claim 17, wherein the cellular sample of interest is a single cell.

19. The method according to claim 17, wherein the cellular sample of interest is a tumor sample.

20. The method according to claim 15, wherein determining the copy number of the one or more nucleic acids of interest present in the nucleic acid sample is based on a ratio of the number of sequencing reads corresponding to the one or more nucleic acids of interest present in the nucleic acid sample to the number of sequencing reads corresponding to the copy number stable genes.

* * * * *